(12) United States Patent
Beals

(10) Patent No.: US 6,617,112 B2
(45) Date of Patent: Sep. 9, 2003

(54) METHODS FOR GENE ARRAY ANALYSIS OF NUCLEAR RUNOFF TRANSCRIPTS

(75) Inventor: Thomas P. Beals, Medford, MA (US)

(73) Assignee: Monsanto Technology LLC, St. Louis, MI (US)

( * ) Notice: Subject to any disclaimer, the term of this patent is extended or adjusted under 35 U.S.C. 154(b) by 0 days.

(21) Appl. No.: 09/955,869

(22) Filed: Sep. 19, 2001

(65) Prior Publication Data

US 2002/0042076 A1 Apr. 11, 2002

Related U.S. Application Data

(60) Provisional application No. 60/239,456, filed on Oct. 11, 2000.

(51) Int. Cl.$^7$ .......................... C12Q 1/68; C07H 21/02; C07H 21/04; C12N 15/00
(52) U.S. Cl. .......................... 435/6; 536/23.1; 536/24.3; 935/76; 935/77; 935/78
(58) Field of Search .............................. 435/6; 536/23.1, 536/24.3; 935/76, 77, 78

(56) References Cited

U.S. PATENT DOCUMENTS 6,261,760 B1 * 7/2001 Fielding
6,468,476 B1 * 10/2002 Friend et al.

OTHER PUBLICATIONS

Schena M., BioEssays 18 (5) : 427–431(May 1996).*
Lockhart et al., Nature 405 :827–836 (Jun. 2000).*
DeRisi et al., Science 278 : 680–686 (Oct. 1997).*
Lockhart et al., Nature Biotechnology 14 : 1675–1680 (Dec. 1996).*
Schena et al., Science 270 : 467–470 (Oct. 1995).*
Hill, Caroline S., et al, Growth Factors and Gene Expression: Fresh Insights from Arrays, www.stke.org/cgi/content/full/OC_sigtrans:1999/3/pe1(Oct. 12, 1999).
Vorst, Oscar et al., "Light–regulated expression of the Arabidopsis thaliana ferredoxin A gene . . . ", The Plant Journal (1993) 3 (6), 793–803.
Berry–Lowe, Sandra A. et al., "Transcriptional Regulation of a Gene Encoding the Small Subunit . . . ", Molecular and Cellular Biology, Aug. 1985, p 1910–1917.
Silverthorne, Jane et al., "Post–transcriptional Regulation of Organ–Specific Expression of Individual rbcS mRNAs in Lemna gibba", The Plant Cell, vol. 2, 1181–1190 Dec. 1990.
Feinbaum Rhonda L. et al., Transcriptional Regulation of the Arabidopsis thaliana Chalcone Synthase Gene, Molecular Cell Biology, May 1988, p. 1985–1992.
Pilgrim, Marsha L. et al., "Circadian and light–regulated expression of nitrate reductase in Arabidopsis", Plant Molecular Biology, 23:349–364, 1993.

* cited by examiner

*Primary Examiner*—Ethan Whisenant
(74) *Attorney, Agent, or Firm*—Thomas E. Kelley

(57) ABSTRACT

Methods for determining transcription rate of mRNA in eukaryotic cells using nuclear runoff transcription where labeled RNA molecules are hybridized against an array of at least 500 nucleic acid molecule probes representing at least part of the genome of the native eukaryotic organism to identify the quantity of nascent mRNA transcripts in said cells. The method can be used to simultaneously identify the quantity of a large number of mRNA transcripts. A rate of degradation for distinct mRNA in a eukaryotic cell rate is determined by comparing a steady state mRNA with nuclear runoff mRNA. Steady state to nuclear runoff ratios are used to determine gene and mRNA structure function relations that leads to gene expression and mRNA stability, predict structural determinants for mRNA stability and predict regulatory motifs for transcription rates. Methods of constructing recombinant organisms with enhanced stability for mRNA expressed from a gene of interest comprise introducing into the genome of an organism a gene containing one or more sequence elements that confer structural stability on mRNA transcribed from said gene.

6 Claims, 2 Drawing Sheets

METHODS FOR GENE ARRAY ANALYSIS OF NUCLEAR RUNOFF TRANSCRIPTS

This application claims the benefit of provisional application No. 60/239,456 filed Oct. 11, 2000.

Current transcriptional profiling methods measure steady state mRNA levels in cells. Steady state message levels reflect the balance of gene expression (as transcription rate) to mRNA decay rate. Nuclear runoff assays measure transcription rates directly. I have discovered and disclose the utility of nuclear runoff assays to generate labeled transcript mRNA hybridization probes for use with transcription profiling arrays. This invention discloses and provides improvements in analyzing transcription of mRNA in eukaryotic cells using nuclear runoff transcription assays, including analysis of nuclear runoff transcription products by microarrays containing genes of interest, e.g. microarrays of nucleic acid molecules representing a genome of interest.

BACKGROUND OF THE INVENTION

Transcription profiling with labeled cDNA probes made by reverse transcription of oligo-dT-primed, whole-cell, total RNA measures steady state mRNA levels. Post transcriptional processes, for example, different mRNA decay rates, make steady state mRNA levels poor predictors of transcription rates. In nuclear runoff experiments isolated nuclei, in which transcription units are paused in the transcription process, are allowed to resume transcription in the presence of radiolabeled nucleotides, thereby labeling the nascent transcripts. Nuclear runoff labeled transcripts hybridized to immobilized DNA elements in the form of transcription profiling arrays containing most or all of the genes in an organism of interest have the potential to measure transcription rates on a whole genome basis. Such nuclear runoff transcription profiling has a variety of applications, e.g. in finding regulatory elements, in predicting mRNA stability from gene and mRNA structure and in constructing enhanced transgenic organisms.

Transcription profiling results from steady state mRNA measurements have been used in attempts to define genomic motifs that contribute to regulation of gene expression. See, for instance, Tavazoie et al., Nat Genet July 1999; 22(3):281–5. Post-transcriptional processes could confound such attempts. Nuclear runoff transcription profiling that is a predictor of transcription rate allows more accurate prediction of regulatory motifs. Knowledge of regulatory motifs that control gene expression can facilitate the design of recombinant organisms containing transgenes that are expressed only in specified cell types at specified times, e.g. in the light, in the dark, in drought or other stress.

The structural features that determine mRNA stability are not well known. See, for instance, Ohme-Takagi et al., Proc Natl Acad Sci USA, 90:24, pages 11811–5 (1993). Steady-state mRNA abundance equals the balance between message synthesis (that is, gene expression measured as transcription rate) and mRNA decay. See Hargrove, et al., Bioessays, 13(12), p. 667–674 (1991). Nuclear runoff transcription profiling together with steady state transcript profiling allows derivation of transcriptome estimates of mRNA decay rates. Such results combined with gene- and mRNA-structure predictions from large scale cDNA sequencing and whole genome sequencing allows correlation of mRNA structure with the derived mRNA decay rate.

Knowledge of structural aspects of mRNA that control mRNA stability can facilitate the design of a very stable mRNA message that can accumulate to high levels in a cell type for which only a weak cell-type-specific promoter was available. History and Methodology of Nuclear Runoff Assays Nuclear runoff methods have found limited utility in prior practice as indicated by the following citations. For instance, newly transcribed mRNA can be identified using the nuclear runoff transcription assay, e.g. as described in Unit 4.10 contributed by Michael E. Greenberg and Timothy P. Bender to "Current Protocols in Molecular Biology" (1997) John Wiley & Sons, Inc., incorporated herein by reference. Nuclear runoff transcription is a procedure for measuring gene transcription as a function of cell state. In a typical method nuclei are first isolated from cultured cells or tissues so as to pause (but not kill) cellular processes including the extension of nascent mRNA transcripts. Isolated nuclei are incubated with labeled nucleoside triphosphate, e.g. $^{32}P$ uridine triphosphate ($^{32}P$-UTP), and unlabelled nucleic acid triphosphates (NTPs) to label nascent mRNA transcripts. Labeled RNA is isolated and used to determine specific RNA transcript levels by hybridization to cDNA probes immobilized on nitrocellulose membrane.

The nuclear runoff transcription assay allows direct measurement and comparison of specific gene transcription in cells in various states of growth or differentiation in contrast to methods that measure steady state levels of mRNA. The nuclear runoff assay is often used with a steady state assay, e.g. northern blot, RNA gel blot, slot blot or dot blot, to assess whether changes in mRNA levels of a particular gene that occur as a function of cell state reflect a change in its synthesis as opposed to a change in mRNA degradation or transport from the nucleus to the cytoplasm. For reviews of nuclear runoff transcription methods, see Marzluff, W. F. Methods Cell Biol., 19:317–331, 1978; Marzluff, W. F. and Huang, R. C. C. Transcription and Translation: A Practical Approach (B. D. Hames and S. J. Higgins, eds.) pp 89–129 IRL Press, Oxford; Greenberg, M. E. and Ziff, E. B., Nature 311:433–438, 1984; and Groundine, M., et al. Mol. Cell. Biol. 1:281–288, 1981, the disclosures of all of which are incorporated herein by reference.

For instance, Berry-Lowe et al., Molecular and Cellular Biology, 5:8, 1910–1917, 1985, discloses the use of nuclear runoff analysis of ribulose-1,5-biphosphate carboxylase where nuclear RNA transcribed in vitro was labeled with [$\alpha$-$^{32}P$]UTP, isolated, and used to probe Southern blots and dot blots containing various DNA samples. Silverthorne et al., The Plant Cell, 2:1181–1190, 1990 disclose the use of nuclear runoff transcriptional analysis to study organ specific expression of the small subunit (SSU) of ribulose-1,5-biphosphate carboxylase/oxygenase. Slot blots of SSU DNA probes were hybridized to in vitro labeled transcripts from root and frond nuclei. And, Pilgrim et al., Plant Molecular Biology, 23:349–364, 1993 disclose the use of nuclear runoff transcriptional analysis to study circadian and light-regulated expression of nitrate reductase in Arabidopsis where plant leaf tissue was harvested at three hour intervals. Nuclei were then allowed to continue transcription in the presence of labeled nucleoside triphosphates to produce labeled RNA transcripts. The labeled RNA transcripts were hybridized to just three DNA targets on a slot blot. In these methods the number of genes that can be monitored is limited by the northern blot or slot blot size. Thus, the nuclear runoff transcription methods were limited in that significant trial and error, or a priori knowledge, was required to select genes which may hybridize to specific RNA transcripts.

OBJECTS OF THE INVENTION

An object of this invention is to provide improved methods for a more rapid, efficient and extensive analysis of RNA transcription rates.

Another object of this invention is to provide methods for determining genome-scale transcription rate of mRNA production in eukaryotic cells.

Another object of this invention is to provide data to allow more accurate prediction of regulatory motifs that influence gene expression.

Yet another object of this invention is to provide methods for constructing a recombinant organism containing a transgene that is specifically expressed in a cell type or in an environmental condition of interest.

Still another object of this invention is to provide methods for finding gene and mRNA structural elements that predict the structural basis and structural determinants of mRNA stability.

Still yet another object of this invention is to provide methods for constructing a recombinant organism with enhanced stability for mRNA transcribed from a gene of interest.

SUMMARY OF THE INVENTION

This invention contemplates and provides a method for determining transcription rate of mRNA in select eukaryotic cells using nuclear runoff transcription where labeled RNA molecules are hybridized against an array of at least 500 nucleic acid molecule probes representing at least part of the genome of the native eukaryotic organism for said cells to identify the quantity of nascent mRNA transcripts in said cells. In preferred aspects of this invention the method is used to simultaneously identify the quantity of at least 100 mRNA transcripts.

This invention also contemplates and provides a method for determining a rate of degradation for distinct mRNA in a eukaryotic cell rate by comparing a steady state level of said mRNA with a rate of synthesis of said mRNA, where nuclear runoff methods are used to determine the rate of synthesis.

This invention also contemplates a method for determining a rate of degradation for a distinct mRNA in proportion to a rate of expression for the corresponding gene in a eukaryotic cell.

This invention also provides methods for determining the gene and mRNA structure-function relations that lead to gene expression and mRNA stability. More particularly, this invention provides a method for predicting the structural determinants for mRNA stability by determining the rates of mRNA degradation and then comparing sequence elements of differentially stable mRNAs to identify the structural determinants. This invention also provides a method for predicting regulatory motifs for transcription rates comprising comparing sequence elements of differentially regulated genes encoding said mRNA molecules to identify the regulatory motifs.

This invention further provides a method of constructing recombinant organisms with enhanced characteristics, including enhanced stability for mRNA transcribed from a gene of interest, comprising introducing into the genome of the organism genetic nucleic acid molecules containing one or more sequence elements that confer desired gene expression patterns that confer structural stability on mRNA.

DETAILED DESCRIPTION OF PREFERRED EMBODIMENTS

Figure 1:
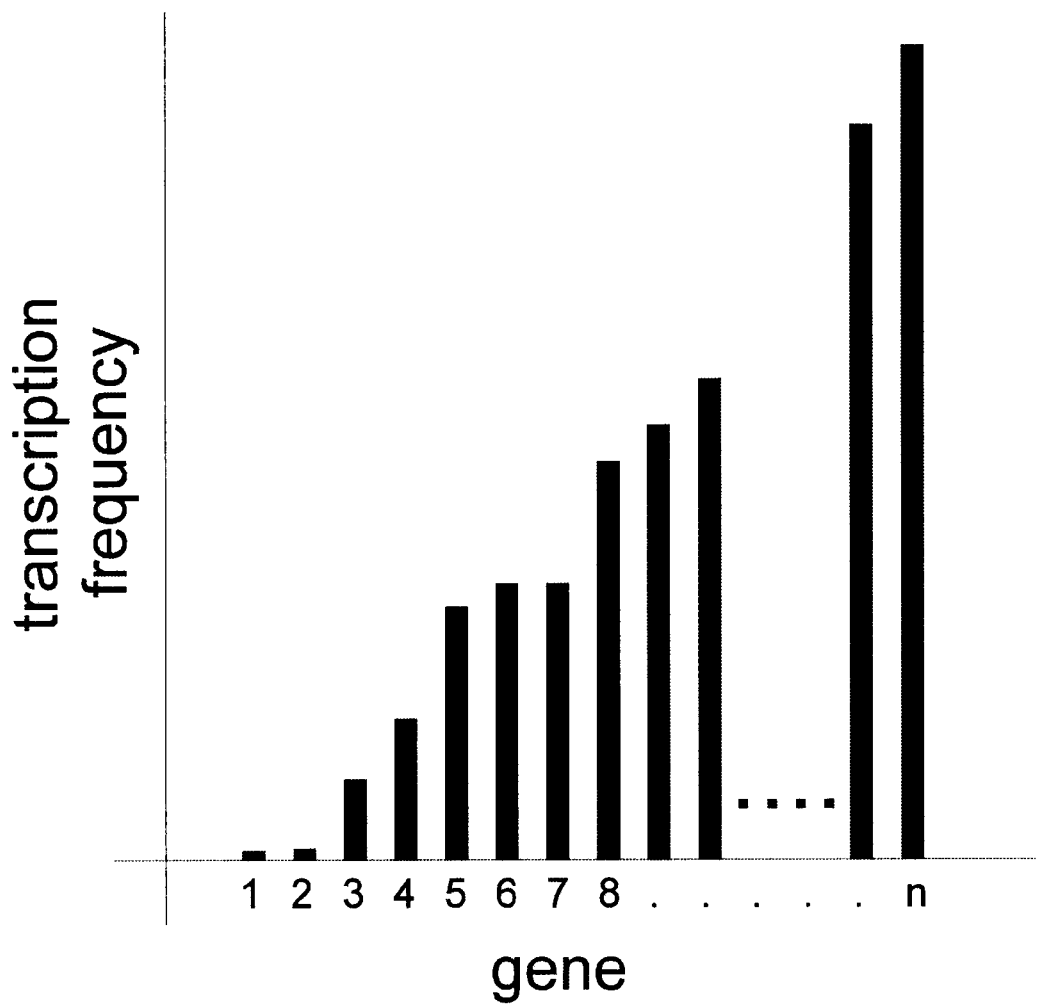
FIG. 1 is a histogram illustrating transcription frequency of a plurality of genes.

The term "nascent mRNA transcript" as used herein means an mRNA precursor molecule that is partially transcribed.

The term "nuclear runoff transcription assay" as used herein means methods for resuming a paused transcription of mRNA in the presence of labeled and unlabelled NTPs to produce completely transcribed, labeled mRNA molecules which can be hybridized to known DNA probes. More particularly, nuclear runoff transcription assay includes the methods which are described by Michael E. Greenberg and Timothy P. Bender in Unit 4.10 of "Current Protocols in Molecular Biology" (1997) John Wiley & Sons, Inc., incorporated herein by reference, and derivative methods specifically described herein.

The term "nucleic acid molecule" as used herein means a DNA or RNA molecule ranging in length from oligonucleotides to full length genes or other large fragments of a genome.

The term "oligonucleotide" as used herein refers to short nucleic acid molecules useful, e.g. for hybridizing probes or nucleic acid molecule array elements. While an oligonucleotide can comprised as few as two nucleotides, i.e. deoxyribonucleotides or ribonucleotides, the exact size will depend on many factors, which in turn depend on the ultimate function or use of the oligonucleotide. When used in microarrays for hybridization oligonucleotides can comprise natural nucleic acid molecules or synthesized nucleic acid molecules and comprise between 5 to 150 nucleotides or preferably about 15 and about 100 nucleotides, more preferably between 15 to 30 nucleotides or most preferably between 18–25 nucleotides complementary to mRNA.

The terms "probe" and "target" as used to describe nucleic acid molecules involved in hybridization are sometimes interchanged which leads to confusion. As used herein the term "probe" refers to an identified nucleic acid molecule and "target" refers to one or more unidentified nucleic acid molecules which can be identified by their hybridization to a probe. In the methods of this invention, labeled mRNA targets are typically hybridized to cDNA probes immobilized on solid arrays, e.g. at least about 500 cDNA probes immobilized in a high density array on a nylon or glass rigid surface, more preferably at least about 1000 or 2000 cDNA probes or higher, e.g. at least about 4000 cDNA probes immobilized in an array on a rigid surface.

As used herein an "array of nucleic acid molecules", e.g. an array of cDNA probes, refers to a solid substrate with nucleic acid molecules located thereon. Several methods have been described for fabricating high density arrays of nucleic acid molecules, often called "microarrays", and using such microarrays in detecting nucleic acid sequences. For instance, microarrays can be fabricated by spotting nucleic acid molecules, e.g. genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Useful substrates for arrays include nylon, glass and silicon. See, for instance, U.S. Pat. Nos. 5,202,231; 5,242,974; 5,384,261; 5,405,783; 5,412,087; 5,424,186; 5,429,807; 5,436,327; 5,445,934; 5,472,672; 5,525,464; 5,527,681; 5,529,756; 5,532,128; 5,545,531; 5,554,501; 5,556,752; 5,561,071; 5,571,639; 5,593,839; 5,599,695; 5,624,711; 5,658,734; 5,700,637; 5,744,305;

5,800,992; 6,004,755 and 6,087,102 the disclosures of all of which are incorporated herein by reference in their entireties.

Sequences can be efficiently analyzed by hybridization to a large set of oligonucleotides or cDNA molecules representing a large portion of the genes of a genome. An array consisting of oligonucleotide probes or cDNA probes which are complementary to sub-sequences of a target sequence can be used to determine the identity of a target sequence, measure its amount, and detect differences between the target and probe sequence.

As used herein the term "transcriptome" of an organism means a major part or, preferably, substantially all of the mRNA molecules which are transcribed from the DNA of the organism. The transcriptome is understood to be a subset of the genome of an organism as it represents mRNA which is transcribed from that part of the DNA which is complementary to the transcribed part of the DNA.

As used herein the term "complete mRNA molecule" means a fully transcribed mRNA molecule as produced naturally in a cell or an mRNA molecule of equivalent (or lesser) length containing labeled nucleoside triphosphate.

The term "recombinant" as used herein describes a molecule which can replicate or function in a living cell although it has been modified by human intervention, e.g. by addition, deletion or substitution of nucleotide or amino acid components. Recombinant molecules include those which are constructed or manipulated outside of the cell. A recombinant organism means an organism with recombinant molecules.

As used herein "transformation" means a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome and to cells which transiently express the inserted DNA or RNA for limited periods of time.

As used herein "transgenic cell" means a cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant. A transgenic plant is a plant or progeny thereof derived from a transformed plant cell or protoplast where the plant DNA contains an introduced exogenous DNA molecule not originally present in a native, non-transgenic plant of the same strain.

The present invention also encompasses the use of nucleic acid molecules comprising regulatory motifs and structural determinants identified by the methods of the present invention in recombinant constructs, e.g. to provide enhanced stability to mRNA. Such nucleic acid molecules are provided in constructs used in recombination which may contain at least two regions of a protein encoding sequence harboring a heterologous portion of DNA such as an antibiotic resistance marker in addition to the encoding segment of interest which can include regulatory element, promoter or partial promoter and a desired protein encoding region. The recombinant vector of this invention may be any vector which can be conveniently subjected to recombinant DNA procedures. The choice of a vector will typically depend on the compatibility of the vector with the host cell into which the vector is to be introduced. The vector may be a linear or a closed circular plasmid. Examples of a method for homologous recombination using a linear vehicle is electroporation of linear DNA and a defective lambda prophage as described in Yu, Daiguan et al Proc. Natl. Acad. Sci. USA (2000), 97(11) pages 5978–5983 or linear DNA and phage lambda Red recombinase, see Wanner, Barry et al, Proc. Natl. Acad. Sci. U.S.A. (2000), 97(12), 6640–6645. The vector system may be a single vector or plasmid or two or more vectors or plasmids which together contain the total DNA to be introduced into the genome of the host. Methods of introduction of recombinant vectors into Agrobacterium species have been described and include triparental mating (Ditta et al. (1985) Plasmid 13:149–153; Ditta et al. (1980) Proc. Natl. Acad. Sci. USA 77:7347–7351) and electroporation (White et al. (1995) Meth. in Mol. Biol. 47:135–141).

The vectors of the present invention preferably contain one or more selectable markers which permit easy selection of transformed cells. A selectable marker is a gene whose product provides, for example, biocide or viral resistance, resistance to heavy metals, prototrophy to auxotrophs, and the like. Various selectable markers may be used depending upon the host species to be transformed, and different conditions for selection may be used for different hosts.

Those vectors of the present invention used for homologous recombination are preferably suicide vectors. As used herein "suicide vector" means a vector without an origin of replication or a vector with an origin of replication that does not work in the target organism (it may be an *E. coli* origin of replication for amplification of the plasmid prior to use in the target organism which is not *E. coli*).

In one aspect of this invention which provides a method for determining transcription of mRNA select eukaryotic cells are isolated from tissue and stored under conditions in which transcription is stopped, e.g. by freezing in liquid nitrogen or in the case of plants by chilling to at least 4° C. Such cells, if alive and active when harvested, will inherently contain nascent mRNA transcripts.

The nascent mRNA can be used to produce labeled mRNA indicative of the extent of ongoing transcription at the time when transcription was paused, e.g. when tissue is harvested and transcription is stopped. For instance, labeled RNA, e.g. fluorescent or $^{32}$P-labelled RNA, can be produced using the nascent mRNA as a template by incubating the nuclei in a cell-simulating environment containing a fluorescent- or $^{32}$P-labeled nucleoside triphosphate such as $^{32}$P-UTP and unlabelled nucleoside triphosphates (NTPs). The labeled RNA molecules can be isolated from the nuclei, purified and allowed to hybridize with an array of nucleic acid molecule probes, e.g. oligonucleotides which are identical to or homologous to nucleic acid sequences of the genome of the eukaryotic organism from which the cells were harvested. For instance, the labeled RNA molecules can be contacted with an array of at least 500 nucleic acid molecules representing genes or open reading frames (ORFs) of the genome of the native eukaryotic organism to identify the quantity of nascent mRNA in said cells. In preferred embodiments of the invention the microarray comprises a sufficiently large number of nucleic acid molecules to permit the simultaneous identification of a plurality of expressed mRNAs, preferably at least about 5 mRNAs, or more, e.g. at least about 10 mRNAs, more preferably at least 15 mRNAs or higher, e.g. at least about 20 mRNAs, most preferably at least about 30 mRNAs. In many cases it may be preferred to simultaneously identify at least about 100 transcribed mRNAs or more, e.g. up to about 200 mRNAs or up to the transcriptome.

Another aspect of this invention provides a method for determining transcription rates for a plurality of mRNA molecules in a eukaryotic cell. In such method nuclei containing paused, nascent mRNA transcripts are incubated in a cell simulating environment comprising labeled uridine triphosphate (UTP) and unlabelled nucleoside triphosphates (NTPs) under conditions in which transcription of the nascent mRNA transcripts is resumed to produce labeled RNA molecules. The production of various RNA species that comprise the labeled RNA after resumed transcription will be proportional to the rate of synthesis for the nascent mRNA at the time transcription is paused. The component amounts of labeled RNA can be determined by analysis of the amount of material hybridized to specific nucleic acid molecules on a microarray. The relative rate of mRNA synthesized can be determined for at least one distinct mRNA or for a plurality of distinct mRNAs, e.g. by hybridizing the related labeled RNA to an array of at least 500 nucleic acid molecule probes, containing at least the complementary DNA to the labeled RNA. The rate of synthesis can be preferably determined for a group of at least 100 mRNAs or larger, e.g. up to the transcriptome level, as illustrated in FIG. 1.

Figure 2:
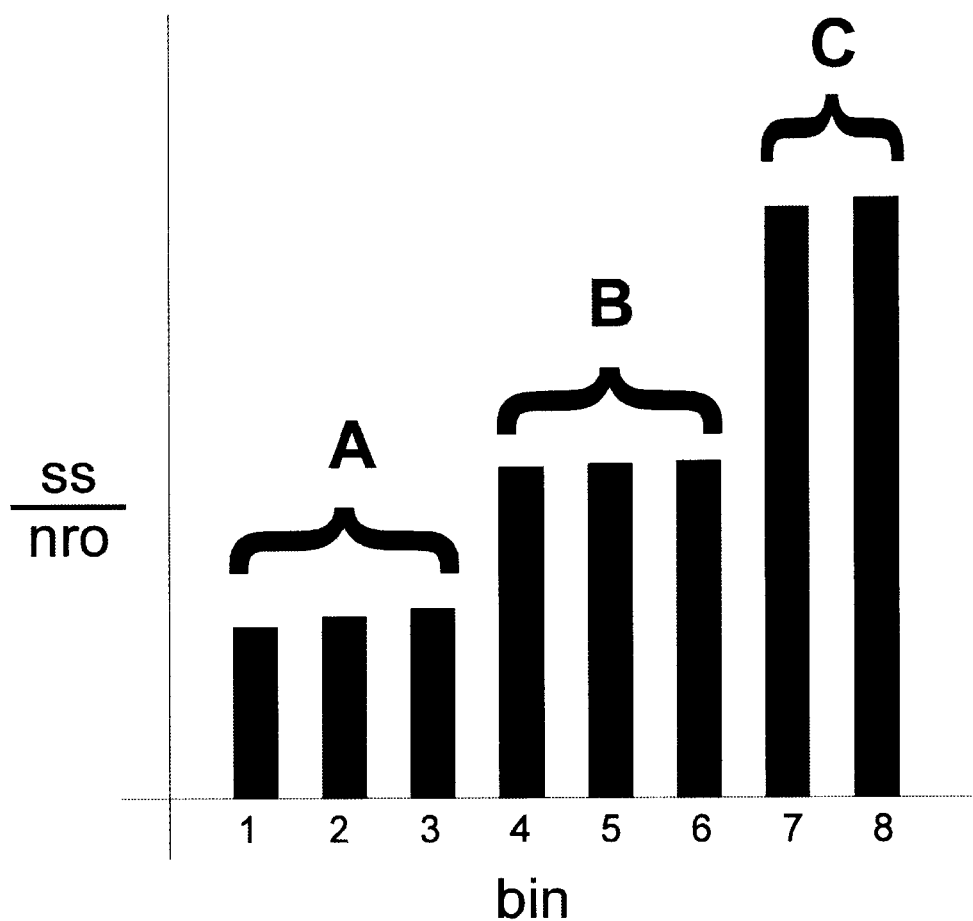
FIG. 2 is a histogram illustrating bins of genes segregated by value of ratio of steady state mRNA level to nuclear runoff mRNA level which is useful in methods of this invention.

In another aspect of this invention a relative rate of mRNA degradation in an eukaryotic cell can be determined as a function of the steady state level of a corresponding mRNA in a cell and the frequency of synthesis of the same mRNA. In such a method tissue can be harvested under conditions in which transcription is temporarily stopped. Nuclei in the harvested tissue can be isolated and separated into a first and second fraction. Nuclei in the first fraction can be labeled and hybridized as discussed above to determine a frequency of synthesis for a plurality of mRNAs. Nuclei in the second fraction can be used to determine a steady state concentration in the cell of the corresponding mRNA, e.g. by hybridizing isolated mRNA to predetermined complementary nucleic acid molecule probes. The rate of mRNA degradation can be determined for a distinct mRNA from a relationship between the steady state concentration of mRNA and the frequency of synthesis of the mRNA. The method is preferably used to determine a rate of degradation for a plurality of mRNAs by hybridizing said related $^{32}$P-labelled RNA to an array of at least 500 nucleic acid molecules; and, more preferably the rate of degradation is simultaneously determined for a group of at least 100 mRNAs, e.g. as illustrated in FIG. 2.

The following materials are use in the examples:
Nucleus Isolation Buffer comprising
  1M sucrose
  10 mM Tris hydrochloride at pH 7.2
  5 mM MgCl$_2$
  10 mM beta-mercaptoethanol.
Percoll solution comprising
  34.23 g of sucrose
  1.0 ml of 1M Tris hydrochloride at pH 7.2
  0.5 ml of 1M MgCl$_2$
  34 microliters of beta-mercaptoethanol and
  Percoll to 100 ml.
Storage Buffer comprising
  20 mM N-2-hydroxyethylpiperazine-N'-2-ethanse sulfonic acid at pH 7.2
  5 mM MgCl$_2$
  2 mM dithiotheritol and
  50% glycerol.
Reaction Buffer comprising
  1 ml of a solution of 10 mM Tris hydrochloride at pH 8
  5 mM MgCl$_2$
  0.3 M KCl
  10 microliters of 100 mM ATP in 0.5 M EDTA at pH 8.0
  10 microliters of 100 mM CTP in 0.5 M EDTA at pH 8.0
  10 microliters of 100 mM GTP in 0.5 M EDTA at pH 8.0
  5 microliters of 1M DTT
  10 microliters of 10 mCi/ml [α-$^{32}$P] UTP.
DNase Solution comprising
  40 microliters of 1 mg/ml RNase-free DNase I (adjusted to pH 5.3 with 0.1M iodoacetic acid/0.15 M sodium acetate)
  1 ml of HSB buffer (0.5 M NaCl, 50 mM MgCl$_2$, 2 mM CaCl$_2$
  10 mM Tris hydrochloride at pH 7.4).
SDS/Tris buffer comprising
  5% (wv) SDS
  0.5 M Tris-hydrochloride at pH 7.4, and
  0.125 M EDTA
Extraction Solution comprising
  25 volumes buffered phenol
  24 volumes chloroform and
  1 volume isoamyl alcohol
DNase I buffer comprising
  20 mM HEPES at pH 7.5
  5 mM MgCl2, and
  1 mM CaCl$_2$
RNase-free DNase I (5 mM) comprising
  0.1 M iodoacetic acid/0.15 M sodium acetate at pH 5.3
  RNase-free DNase I to 1 mg/ml
  1M CaCl$_2$ to final concentration of 5 mM

EXAMPLE 1

This example illustrates the harvesting of plant cells for nuclear runoff assay, e.g. as disclosed by Feinbaum R. L. et al. "Transcriptional Regulation of the *Arabidopsis thaliana* Chalcone Synthase Gene, *Molecular and Cellular Biology*, Vol. 8, No. 5, May 1988, p. 1985–1992, incorporated herein by reference. Leaf tissue from *Arabidopsis thaliana* is washed with cold (i.e. 4° C.) distilled water. The tissue is chopped into small pieces and submerged in cold diethyl ether for 3 minutes, rinsed in cold distilled water and mechanically homogenized in 3 volumes of Nucleus Isolation Buffer. The buffered homogenized tissue is filtered and the filtrate centrifuged in a Beckman JA 10 rotor at 9,000 rpm for 15 minutes. A pellet of the centrifuged solids is suspended in a Dounce homogenizer in 20 ml of the nucleus isolation buffer. Percoll Solution is added to the suspended solids to produce suspension of nuclei at a final solution of 35% (vol/vol) Percoll. The suspended nuclei is layered over 7.5 ml of 60% (vol/vol) Percoll Solution to created discontinuous Percoll gradients which are centrifuged in a Beckman JS 13 rotor at 2,000 rpm for 10 minutes then at 8,000 rpm for 20 minutes. The crude nuclei are harvested from between the 35% and 60% layers and diluted with 5 volumes of the Nucleus Isolation Buffer and then collected by centrifugation. The crude nuclear pellet is suspended in 1.0 ml of Storage Buffer. The buffered crude nuclei suspension is stored at −70° C.

The number of nuclei in each preparation is determined by quantitating the DNA content with diphenylamine analysis where 50 microliter of nuclei in storage buffer is pelletized by centrifugation, the storage buffer is removed and chloroplast pigments are extracted in 200 microliters of acetone. The nuclei are recovered from the acetone extraction by centrifugation and suspended in 0.5 N perchloric acid. The perchloric acid solution of nuclei is boiled for 10 minutes and assayed as described by Burton "Determination of DNA concentration with diphenylamine", *Methods Enzymol.*, 12B: 163–166 (1968), incorporated herein by reference.

EXAMPLE 2

This example illustrates nuclear runoff transcription following procedures described by Greenberg et al. in Current Protocols on Molecular Biology, supra. A sample of $10^7$ nuclei (~2 microgram of DNA by diphenylamine analysis) is used in each nuclear run-on experiment. The nuclei, 200 microliters of Reaction Buffer, and 100 microCi, 760 Ci/mmol $\alpha^{32}$P-dUTP are added to a polypropylene centrifuge tube and incubated for 30 minutes at 30° C. with shaking to produce a solution of nuclei containing labeled transcripts. 0.6 ml of the DNase solution is added to the labeled nuclei, well mixed and incubated for 5 minutes at 30° C.

A mixture of 200 microliters of SDS/Tris Buffer and 10 microliters of 20 mg/ml proteinase K is added and incubated for 30 minutes at 42° C. to provide a solution containing labeled RNA.

EXAMPLE 3

This example illustrates the extraction and precipitation of RNA following procedures described by Greenberg et al. in Current Protocols on Molecular Biology (1997) Unit 4.10, incorporated herein by reference. The RNA-containing solution prepared in Example 2 is extracted in 1 ml of Extraction Solution and centrifuged at 2000 rpm for 5 minutes at room temperature. The aqueous phase is separated and mixed with 2 ml water, 3 ml 10% TCA/60 mM sodium pyrophosphate and 10 microliter of 10 mg/ml *E. coli* tRNA, and then incubated for 30 minutes on ice. The TCA precipitate is filtered on 0.45 micrometer Millipore™ HA paper and washed three times with 10 ml of 5% TCA/30 mM sodium pyrophosphate. The filter is incubated with 1.5 ml of DNase I Buffer and 37.5 microliters of 1 mg/ml RNase-free DNase I for 30 minutes at 37° C. The reaction is stopped by adding 45 microliters of 0.5 M EDTA and 68 microliters of 20% SDS. The sample is heated for 10 minutes to 65° C. to elute RNA. The supernatant containing $^{32}$P-labeled RNA is removed and saved. 1.5 ml of elution buffer is added to the filter and incubated for 10 minutes at 65° C.; the second supernatant is removed and combined with the earlier supernatant. A 3 ml volume of the combined supernatant is mixed with 4.5 microliters of 20 mg/ml proteinase K and incubated for 30 minutes at 37° C. The solution is extracted with 3 ml of Extraction Solution. The aqueous phase is removed to a silanized tube and mixed with 0.75 ml of 1 M NaOH and left on ice for 10 minutes. The reaction is quenched by adding 1.5 ml of 1M HEPES. RNA is precipitated by adding 0.53 ml of 3M sodium acetate and 14.5 ml of ethanol and incubated on dry ice for 30 minutes. RNA is separated by centrifuging at 9000 rpm in a Beckman JA 20 rotor for 30 minutes at 4° C. The RNA pellet is resuspended in 2.5 ml TES solution to provide a processed RNA solution.

EXAMPLE 4

This example illustrates the hybridization of RNA to cDNA. A microarray comprising cDNA is prepared by attaching polynucleotides representing about 6,000 genes of *Arabidopsis thaliana* to defined areas on the surface of a negatively-charged, nylon support membrane. The polynucleotides are amplified cDNA molecules in the range of about 200 to 2000 nucleotide bases in length. The processed RNA solution prepared in Example 3 is mixed with 2.5 ml of TES/NaCl solution and allowed to hybridize to a microarray in a 50 ml chamber rotating at 65° C. in a hybridization oven. The RNA solution is rinsed off the microarray by two 1 hour washings with 2×SSC at 65° C. The microarray is incubated for 30 minutes in an RNase solution, rinsed again for 1 hour in 2×SSC at 37° C., dried and placed in contact with a Fuji Phoshoimager™ imaging screen. After an appropriate exposure time the array image is read as a digital file representing the hybridization intensity from each array element which is proportional to the mRNA transcription rate for each gene. The transcription rates are sorted and presented graphically as illustrated in FIG. 1.

EXAMPLE 5

This example illustrates measurement of steady-state mRNA levels. A sample of same leaf tissue as used in Example 1 is mechanically ground while frozen in liquid nitrogen. The steady-state mRNA is isolated from ground tissue using commercially available reagents, such Dynabeads™ mRNA DIRECT™ from Dynal Biotech, Oslo, Norway. The isolated mRNA is labeled by random oligonucleotide priming, e.g. with a Superscript™ First Strand Synthesis System for RT PCR, with labeled dCTP, from Invitrogen Corporation, Carlsbad, Calif. The labeled first strand cDNA is hybridized to an array and hybridization signals read as in Example 4 indicate steady state mRNA levels. The ratios of the steady-state signal from the first-strand cDNA-probed arrays to the nuclear runoff signals from labeled mRNA as determined in Example 4 are sorted and presented graphically as illustrated in FIG. 2.

APPLICATIONS

FIG. 1 illustrates conceptually the expected results from transcriptome nuclear-runoff labeled-mRNA-probed microarrays. The microarray element signals corresponding to gene expression-mRNA transcription are sorted and plotted on a histogram. For any given tissue and environmental condition, some genes are expected to be not transcribed and other genes will be highly transcribed.

Highly expressed genes may share, or may be divided into subgroups that share, regulatory motifs. Identification of regulatory motifs among genes that have in common high expression rates in specific tissues or environmental conditions have been described. See Tavazoie et al., Nat Genet July 1999; 22(3): 281–5, which is incorporated herein by reference in its entirety, for a disclosure of computational algorithms that are known in the art for statistical characterization of sequence elements to discover and identify regulatory motifs and structural determinants.

The steady state mRNA levels and the mRNA transcription rates can be used to determine a rate of degradation for mRNA, e.g. by comparing element by element signals for each array element in both of the steady state and nuclear runoff hybridizations. The relative ratio difference between the steady state hybridization signal and the nuclear runoff hybridization signal will indicate the relative degradation rates for mRNA transcribed by each gene represented on the array.

The relative value of the signal ratios, i.e. steady state hybridization signal to nuclear runoff hybridization signal (ss/nro), for each gene represented on the array can be arranged in order and segregated into groups of neighbors (bins), e.g. as illustrated in FIG. 2. If there is no differential post transcriptional regulation, then the element-wise "ss/nro" ratio over all elements would be constant. Differences in "ss/nro" ratios indicate different message stability. The bins of genes with the lowest "ss/nro" ratios, e.g. the Group A bins of FIG. 2, indicates the least stable transcript; the highest "ss/nro" ratio, e.g. the Group C bins of FIG. 2, indicates the most stable transcript. Thus, genes corresponding to high "ss/nro" ratios are candidates for identifying structural motifs contributing to mRNA stability; and genes corresponding to low "ss/nro" ratios are candidates for identifying structural motifs contributing to low mRNA stability. In addition, the mRNAs corresponding to a group of high ratio assays are candidates for use in predicting structural determinants of mRNA stability. Such structural determinants are useful in constructing recombinant organisms with enhanced mRNA stability.

It is especially useful to determine "ss/nro" ratios for various conditions affecting the organism. In the case of plants useful conditions for variance include nitrogen feeding, circadian time pints, sugar sensing, etc. Comparing "ss/nro" ratios for the various conditions allows a determination of genes with regulatory motifs of interest in response to the condition. For instance, it is expected that different classes of genes will generally change ratios in the same manner as conditions change.

What is claimed is:

1. A method for analyzing mRNA molecules in a eukaryotic cell, said method comprising
   (a) pausing transcription in select eukaryotic cells containing nuclei with nascent mRNA transcripts,
   (b) using labeled mRNA transcripts show a relative rate of synthesis for a plurality of mRNA molecules,
   (c) determining a frequency of synthesis for a plurality of said mRNA transcripts,
   (d) using at least part of said cells to determine a steady-state level of mRNA at the time of said pausing; and
   (e) determining relative rates of mRNA degradation for mRNA transcripts by comparing frequencies of synthesis and steady-state concentrations.

2. A method according to claim 1 wherein the rate of degradation is determined simultaneously for at least 100 mRNA molecules.

3. A method according to claim 1 wherein said rate of mRNA degradation is determined for a plurality of related mRNAs by hybridizing said labeled RNA to an array of at least 500 nucleic acid molecules.

4. A method according to claim 3 wherein the rate of mRNA degradation is simultaneously determined for a group of at least 100 related mRNAs.

5. A method for predicting regulatory motifs for transcription rates, comprising:
   (1) finding transcription rates of mRNA molecules according to claim 1, and
   (2) comparing sequence elements of differentially regulated genes encoding said mRNA molecules to identify regulatory motifs.

6. A method of predicting structural determinants of mRNA stability, comprising:
   (1) determining rates of degradation of mRNA molecules according to claim 1, and
   (2) comparing gene and mRNA sequence elements of differentially stable mRNAs to identify structural determinants.

* * * * *